(12) United States Patent
Lahiji et al.

(10) Patent No.: US 10,238,362 B2
(45) Date of Patent: Mar. 26, 2019

(54) INTEGRATED WEARABLE DEVICE FOR DETECTION OF FETAL HEART RATE AND MATERIAL UTERINE CONTRACTIONS WITH WIRELESS COMMUNICATION CAPABILITY

(75) Inventors: Rosa R. Lahiji, Augusta, GA (US); Masoud Roham, San Diego, CA (US); Mehran Mehregany, San Diego, CA (US)

(73) Assignee: GARY AND MARY WEST HEALTH INSTITUTE, La Jolla, CA (US)

( * ) Notice: Subject to any disclaimer, the term of this patent is extended or adjusted under 35 U.S.C. 154(b) by 0 days.

(21) Appl. No.: 13/094,678

(22) Filed: Apr. 26, 2011

(65) Prior Publication Data

US 2012/0065479 A1   Mar. 15, 2012

Related U.S. Application Data

(60) Provisional application No. 61/327,875, filed on Apr. 26, 2010.

(51) Int. Cl.
*A61B 5/00* (2006.01)
*A61B 8/00* (2006.01)
(Continued)

(52) U.S. Cl.
CPC ........ *A61B 8/4236* (2013.01); *A61B 5/02411* (2013.01); *A61B 5/4362* (2013.01); *A61B 8/4427* (2013.01); *A61B 8/4472* (2013.01); *A61N 7/00* (2013.01); *A61B 5/04882* (2013.01); *A61B 5/4325* (2013.01); *A61B 8/02* (2013.01); *A61B 8/06* (2013.01); *A61B 8/0866* (2013.01); *A61B 8/0883* (2013.01); *A61B 8/0891* (2013.01); *A61B 8/488* (2013.01); (Continued)

(58) Field of Classification Search
CPC .......................... A61B 5/02427; A61B 5/4362
USPC ................ 600/301, 437, 438, 450, 453, 459
See application file for complete search history.

(56) References Cited

U.S. PATENT DOCUMENTS 4,640,295 A   2/1987  Isaacson
5,257,627 A   11/1993  Rapoport
(Continued)

OTHER PUBLICATIONS

Advanced Pharma, "Huntleigh Tele-Fetal Monitors" as of Apr. 2011, 2 pages. http://www.advanced-pharma.com/fetalmonitors.html, © 2004.
(Continued)

*Primary Examiner* — Rochelle Turchen
(74) *Attorney, Agent, or Firm* — David B. Murphy; O'Melveny & Myers LLP (57) ABSTRACT

A wearable patch is provided for use on the body which preferably comprises an ultrasound sensor array, a transmission system coupled to the ultrasound sensor array adapted to provide signal information for ultrasound transmission into the body, and a receiver system coupled to the ultrasound sensor array adapted to receive signal information from the reflected ultrasound signal received from the body. A control circuitry is coupled to the transmission system and the receiver system. The patch is preferably provided with a wireless communication system to permit external control and or communication. Applications range from diagnostics and monitoring, to rehabilitation and wound healing.

32 Claims, 3 Drawing Sheets

(51) Int. Cl.
*A61B 5/024* (2006.01)
*A61N 7/00* (2006.01)
A61B 5/0488 (2006.01)
A61B 8/02 (2006.01)
A61B 8/08 (2006.01)
A61B 8/06 (2006.01)

(52) U.S. Cl.
CPC ............ *A61B 8/5207* (2013.01); *A61B 8/565* (2013.01); *A61B 2560/0412* (2013.01)

(56) References Cited

U.S. PATENT DOCUMENTS

| | | | |
|---|---|---|---|
| 5,363,857 | A | 11/1994 | Howard |
| 5,544,665 | A | 8/1996 | Litovitz et al. |
| 5,807,271 | A | 9/1998 | Tayebi et al. |
| 5,817,035 | A | 10/1998 | Sullivan |
| 5,882,300 | A | 3/1999 | Malinouskas et al. |
| 6,115,624 | A | 9/2000 | Lewis et al. |
| 6,264,614 | B1 | 7/2001 | Albert et al. |
| 6,416,471 | B1 | 7/2002 | Kumar |
| 6,781,522 | B2 | 8/2004 | Sleva et al. |
| 6,955,650 | B2 | 10/2005 | Mault et al. |
| 7,162,278 | B2 | 1/2007 | Vanselous |
| 7,257,438 | B2 | 8/2007 | Kinast |
| 7,277,745 | B2 | 10/2007 | Natarajan et al. |
| 7,333,850 | B2 | 2/2008 | Marossero et al. |
| 7,470,232 | B2 | 12/2008 | Hoctor et al. |
| 7,532,923 | B1 | 5/2009 | Hayes-Gill et al. |
| 7,593,765 | B2 | 9/2009 | Rapoport et al. |
| 7,758,522 | B2 | 7/2010 | Pandit |
| 7,764,996 | B2 | 7/2010 | Zhang et al. |
| 7,865,233 | B2 | 1/2011 | Haefner |
| 7,976,480 | B2 | 7/2011 | Grajales et al. |
| 8,066,379 | B2 | 11/2011 | Lalley et al. |
| 8,116,841 | B2 * | 2/2012 | Bly et al. ............ 600/391 |
| 8,116,855 | B2 | 2/2012 | James et al. |
| 8,125,440 | B2 | 2/2012 | Guyot-Sionnest et al. |
| 8,229,550 | B2 | 7/2012 | James et al. |
| 8,255,238 | B2 | 8/2012 | Powell et al. |
| 8,273,370 | B2 | 9/2012 | Harima et al. |
| 8,280,484 | B2 | 10/2012 | Boyden et al. |
| 8,301,232 | B2 | 10/2012 | Albert et al. |
| 8,332,021 | B2 | 12/2012 | Vullings et al. |
| 8,348,841 | B2 | 1/2013 | Varadan |
| 2004/0203354 | A1 | 10/2004 | Yue |
| 2005/0090725 | A1* | 4/2005 | Page .................. A61B 5/0059 600/344 |
| 2005/0102167 | A1 | 5/2005 | Kapoor |
| 2005/0251044 | A1* | 11/2005 | Hoctor et al. ............ 600/444 |
| 2007/0016089 | A1 | 1/2007 | Fischell et al. |
| 2007/0106133 | A1 | 5/2007 | Satchwell et al. |
| 2007/0149887 | A1 | 6/2007 | Hwang et al. |
| 2007/0191728 | A1 | 8/2007 | Shennib |
| 2007/0208252 | A1 | 9/2007 | Makower |
| 2007/0255184 | A1* | 11/2007 | Shennib ............ 600/591 |
| 2007/0299349 | A1 | 12/2007 | Alt et al. |
| 2008/0039744 | A1 | 2/2008 | Hamilton |
| 2008/0064980 | A1 | 3/2008 | Lee et al. |
| 2008/0114219 | A1* | 5/2008 | Zhang et al. ............ 600/301 |
| 2008/0114224 | A1* | 5/2008 | Bandy et al. ............ 600/302 |
| 2008/0119705 | A1 | 5/2008 | Patel et al. |
| 2009/0143650 | A1 | 6/2009 | Guion-Johnson |
| 2009/0303098 | A1 | 12/2009 | Wilkins |
| 2009/0318802 | A1* | 12/2009 | Boyden et al. ............ 600/437 |
| 2010/0049050 | A1 | 2/2010 | Pelissier et al. |
| 2010/0055162 | A1* | 3/2010 | Harima et al. ............ 424/449 |
| 2010/0106519 | A1 | 4/2010 | Lemke et al. |
| 2010/0274145 | A1 | 10/2010 | Tupin, Jr. et al. |
| 2010/0316231 | A1* | 12/2010 | Williams .............. H04R 3/005 381/92 |
| 2011/0077526 | A1* | 3/2011 | Zwirn ............ 600/459 |
| 2011/0137209 | A1 | 6/2011 | Lahiji et al. |
| 2011/0251469 | A1* | 10/2011 | Varadan ............ 600/301 |
| 2012/0065479 | A1 | 3/2012 | Lahiji et al. |
| 2012/0150010 | A1 | 6/2012 | Hayes-Gill et al. |
| 2012/0232398 | A1 | 9/2012 | Roham et al. |

OTHER PUBLICATIONS

Ayat, et al., "Prototype of a Standalone Fetal ECG Monitor," 2010 IEEE Symposium on Industrial Electronics and Applications (ISIEA 2010), Oct. 3-5, 2010, pp. 617-622.

Azhim, et al., "Monitoring Carotid Blood Flow and ECG for Cardiovascular Disease in Elder Subjects," Engineering in Medicine and Biology Society, 2005, IEEE-EMBS, 2005, 27th Annual International Conference of the 2005, Sep. 1-4, 2005, pp. 5495-5498.

Baby Beat, About Us—Who is Baby Beat?, as of Apr. 2011, 2 pages. http://www.babybeat.com/about-babybeat.html.

Barth, et al., "Tempo 3.1: A Body Area Sensor Network Platform for Continuous Movement Assessment", Wearable and Implantable Body Sensor Networks, 2009, BSN 2009, Sixth International Workshop, 2009, pp. 71-76.

Byl, et al., "Indsional Wound Healing: A Controlled Study of Low and High Dose Ultrasound", JOSPT, vol. 18, No. 5, Nov. 1993, pp. 619-628.

Chen, et al., "A Comparative Study of a New Cardiotocography Analysis Program," Engineering in Medicine and Biology Society, $31^{st}$ Annual International Conference of the IEEE EMBS, Sep. 2-6, 2009, pp. 2567-2570.

Chou, et al., "Radio Frequency Electromagnetic Exposure: Tutorial Review on Experimental Dosimetry", Bioelectricmagnetics, vol. 17, issue 3, 1996, pp. 195-208.

Cox, "Top-Rated Cell Phones Also Rank High in Radiation Emissions", Network World, Feb. 24, 2010, 3 pages. http://www.pcworld.idg.com.au/article/337324/top_rated_cell_phones_also_rank_high_rad . . . .

Espina, et al., Wireless Body Sensor Network for Continuous Cuff-less Blood Pressure Monitoring, Proceedings of the $3^{rd}$ IEEE-EMBS, Internatioal Summer School and symposium on Medical Devices and Biosensors, MIT, Sep. 4-6, 2006, pp. 11-15.

Federal Office of Public Health (FOPH), "Bluetooth", last updated on Jan. 30, 2007, 4 pages. http://www.bag.admin.ch/themen/strahlung/00053/00673/03571/index.html?lang=en.

Fitzpatrick, "Ultrasound imaging now possible with a smartphone," Apr. 20, 2009, 2 pages. http://news-info.wustl.edu/tips/page/normla/13928.html.

GE Healthcare, Ultrasound for Vascular Imaging, as of Apr. 2011, 3 pages. http://www.gehealthcare.com/usen/ultrasound/genimg/products/vascular.htm, © 2010.

GE Healthcare, Ultrasound Product Information, as of Apr. 2011, 2 pages. https://www2.gehealthcare.com/portal/site/usen/menuitem.0668199d894d51503806171047b29330/?vgnextoid=dd3ba52fcea2d110VgnVCM100000258c1403RCRD&vgnextfmt=defaul, © 2011.

GE, Vscan pocket-sized, ultra-smart ultrasound unveiled, Oct. 20, 2009, 3 pages. http://www.gereports.comJvscan-pocket-sized-ultra-smart-ultrasound-unveiled.

GE Healthcare, for the Obstetrics Patient overview of Obstetrics Ultrasound products, as of Apr. 2011, 1 page. http://www.gehealthcare.com/usen/patient/ultrasound/aboutvoluson.html, © 2010.

Ghasemzadeh, et al., "A Greedy Buffer Allocation Algorithm for Power-Aware Communication in Body Sensor Networks", Proceedings of the Eighth IEEE/ACM/IFIP International Conference on Hardware/Software Codesign and System Synthesis, ser. CODES/ISSS '10, New York, N.Y., USA: ACM, 2010, pp. 195-204.

Ghasemzadeh, et al., "Structural Action Recognition in Body Sensor Networks: Distributed Classification Based on String Matching,", IEEE Transactions on Information Technology in Biomedicine, vol. 14, No. 2, Mar. 2010, pp. 425-435.

Gussenhoven, et al., "Arterial Wall Characteristics Determined by Intravascular Ultrasound Imaging: An in Vitro Study," Journal of the American College of Cardiology, vol. 14. No. 4, Oct. 1989, pp. 947-952.

(56) References Cited

OTHER PUBLICATIONS

Haider, "Power Drive Circuits for Diagnostic Medical Ultrasound", Proceedings of the 18th International Symposium on Power Semiconductor Devices & IC's, Jun. 4-6, 2006 8 pages.
Henderson, et al., "A Portable High-intensity Focused Ultrasound Device for Noninvasive Venous Ablation", Journal of Vascular Surgery, 2009, pp. 1-5.
Jafari, et al., "Medical Embedded Systems", Embedded System Design Topics, Techniques and Trends, IFIP Advances in Information and Communication Technology, vol. 231, 2007, pp. 441-444.
Jun, et al., "Wearable ECG Recognition & Monitor", Proceedings of the 18$^{th}$ IEEE Symposium on Computer-Based Medical Systems (CBMS'05), 2005, 6 pages.
Leonov, et al., "Thermoelectric Mems-Generators as a Power Supply for a Body Area Network", The 13$^{th}$ International Conference on Solid-State Sensors, Actuators and Microsystems, vol. 1, Jun. 5-9, 2005, pp. 291-294.
lgmedsupply.com, Professional Ultrasound Unit for Ultrasound Therapy, as of Apr. 2011, 5 pages. http://www.lgmedsupply.com/lgpoulun.html.
Miller, "Two-mic system detects fetal heart rate anomalies, prenatal beat sampling,", 2009, 4 pages. http://www.engadget.com/2009/08/30/two-mic-system-detects-fetal-heart-rate-anomalies-prenatal-beat.
NCC (National Certification Corporation), "NICHD Definitions and Classifications: Application to Electronic Fetal Monitoring Interpretation", NCC Monograph, vol. 3, No. 1, 2010, pp. 1-20.
Park, et al., An Ultra-Wearable Wireless, Low Power ECG Monitoring System, Biomedical Circuits and Systems Conference, 2006, BioCAS, IEEE, Dec. 2006, pp. 241-244.
Schlembach, et al., "Monitoring the Progress of Pregnancy and Labor using Electromyography", European Journal of Obstetrics & Gynecology and Reproductive Biology, vol. 144, Supp. 1, 2009, pp. S33-S39.
Sheehan, et al., "Expert visual guidance of ultrasound for telemedicine", J Telemed Telecare, vol. 16, No. 2, 2010, pp. 77-82.
sonosite.com, Portable Diagnostic Ultrasound Machines as of Apr. 2011, 2 pages. http://www.sonosite.com/products/portable-ultrasound/.
Sweha, et al., "Interpretation of the Electronic Fetal Heart Rate During Labor", American Family Physician, vol. 59, issue 9, May 1, 1999, pp. 2487-2500.
usedultrasound.com, "Acuson P40 Ultrasound System" as of Apr. 2011, 2 pages. http://www.usedultrasound.com/ultrasound-systems/acuson/acuson-p10-ultrasound-system.
van Geijn, "Cardiotocography", in Textbook of Perinatal Medicine, Parthenon Publishing, 1998, vol. 2, pp. 1424-1428. http://www.obgyn.net/displayarticle.asp?page=/fm/articles/cardiotocographya998-def.
wikipedia.org, "Specific Absorption Rate", as of Jul. 24, 2013, 4 pages. http://en.wikipedia.org/wiki/Specific_absorption_rate.
Wildstrom, "Bluetooth: Dangerous Waves?", Bloomberg Businessweek, Apr. 27, 2005, 3 pages,http://www.businessweek.com/technology/content/apr2005.tc20050427-5651.htm.
Willacy, et al., "Intrapartum Fetal Monitoring", Patient.co.uk, emis, document ID: 1063, version 23, last checked Dec. 20, 2010, 6 pages.
World Health Organization, "Electromagnetic Fields and Public Health: Mobile Phones", Fact sheet No. 193, Jun. 2011, 4 pages, http://www/who.int/mediacentre/factsheets/fs193/en/.
Xiao et al., "Transmission Power Control in Body Area Sensor Networks for Healthcare Monitoring", IEEE Journal on Selected Areas in Communications, 2009, vol. 27, No. 1, pp. 37-48.
Zappi, et al., "Activity Recognition from on-Body Sensors: Accuracy-Power Trade-off by Dynamic Sensor Selection", EWSN 2008, LNCS 4913, 2008, pp. 17-33.

\* cited by examiner

INTEGRATED WEARABLE DEVICE FOR DETECTION OF FETAL HEART RATE AND MATERIAL UTERINE CONTRACTIONS WITH WIRELESS COMMUNICATION CAPABILITY

RELATED APPLICATION STATEMENT

This application claims priority to and benefit of U.S. Provisional Application Ser. No. 61/327,875, filed Apr. 26, 2010, entitled "Ultrasound Patch", the content of which is hereby incorporated by reference in its entirety as if fully set forth herein.

FIELD OF THE INVENTION

The present invention relates to methods, apparatus and systems for providing a wearable ultrasound solution in form of a BandAid-type patch for use on a body. More particularly, it relates to a wearable ultrasound patch that may be used for diagnosis, monitoring and rehabilitation of various organs and parts of the body.

BACKGROUND OF THE INVENTION

Ultrasound waves are utilized in many different fields, typically as a tool to penetrate a medium to measure its reflection signature. In medicine, imaging ultrasound devices are usually used for diagnostic medical imaging of internal organs, muscles, tendons and even fetus inside the uterus [1]. Other existing medical applications include monitoring different organs, nerve stimulation, wound healing and rehabilitation [2], [4]-[9].

Traditional ultrasound imaging devices are capable of providing sophisticated live images and enable extraction of characteristic features using advanced signal processing techniques. However, they are generally large, stationary and expensive. Moderate size imaging devices with limited mobility, such as computer-on-wheels systems, are also available with performance generally similar to the larger systems [10]-[11]. More recently, there have been a few introductions of handheld ultrasound imaging devices, such as the GE Vscan [12] and Acuson P10 [13] that feed the need of on-the-go applications. However, none of these devices are wearable or nonintrusive. In a wide range of medical ultrasound diagnostic applications, such as fetal heartbeat monitoring, the ability to continuously monitor the heartbeat is more significant than producing an image of the heart. Fetal heartbeat sensing devices, using ultrasound Doppler, are available in large-size, medical-grade instruments [14] and lower cost, consumer handheld ones [15]-[16]. However, these current solutions are not wearable (due to size) and therefore do not enable continuous monitoring without interfering with the subject's regular activities. They are also expensive compared to the price point possible for the patch-type device disclosed here.

Current therapeutic and rehabilitation ultrasound machines are stationary and require regular visits by the patient due to the gradual and progressive nature of the treatment; sometimes for duration of few months. Patients with known lesions in the carotid artery should also visit the hospital for taking the ultrasound and being monitored regularly depending on the risk factors. Such monitoring also occurs after surgery.

For decades, ultrasound machines were only available in stationary locations in hospitals and were operated by trained technicians for diagnostic applications. Today however, portable and handheld diagnostic ultrasound machines enable doctors to examine their patients at the point of care, whether at bedside or an accident scene [17]. Other types of applications include therapeutic devices of small size that can either be applied by a therapist [12], [18] or at home by the patient for physical therapy, reducing healing time and rehabilitation, or just to reduce pain [19].

The importance of a lighter weight, user friendly and inexpensive ultrasound device for such applications is compelling [7]-[9]. With continuous monitoring of the arteries with an easy-to-apply, wirelessly-powered adhesive patch, the patient can be monitored more closely all the time, eliminating the need for frequent visits to the hospital. In addition, such a device can save lives by detecting the onset of stroke as changes in the shape and size of the lesion is observed. An ultrasound patch, similar in form factor to a medical adhesive patch (e.g., an appropriately-sized BandAid), can be worn by a subject without interfering with the subject's routine activities, allowing continuous monitoring or therapy. The ultrasound data can be recorded on the patch for subsequent download/transmission and/or transmitted in real time (wirelessly) to a nearby portable device, such as a mobile phone, personal digital assistant, or personal computer. In addition to serving as a relay station to (wirelessly) transmit the acquired data to a network of backend servers, analytics and visualization can be made available on the portable device for the benefit of the subject. A network of backend servers usually supports the healthcare providers for further analysis of the data/information or for archiving of the data/information in electronic records. Benefits of such electronic recording, analysis, transmission, and archiving of ultrasound signals is compelling in many settings, including ambulatory, home, office, hospital, and trauma care.

SUMMARY OF THE INVENTION

A wearable patch is provided for use on the body which preferably comprises an ultrasound sensor array, a transmission system coupled to the ultrasound sensor array adapted to provide signal information for transmission into the body, and a receiver system coupled to the ultrasound sensor array adapted to receive ultrasound signal information reflected from the body. A control circuitry is coupled to the transmission system and the receiver system. The patch is preferably provided with a wireless communication system to permit external control and or communication. The ultrasound sensor array preferably has at least 2, and more preferably 4 or 8, transducer elements. The transmission system preferably includes an amplifier adapted to receive an input from the control system, and optionally includes a digital to analog converter disposed between the control system and the amplifier, and an upstream digital signal processor. The receiver system preferably includes an amplifier, most preferably a low noise amplifier. The receive system preferably further includes an analog to digital converter coupled to the amplifier, and a digital signal processor coupled to the digital to analog converter. Preferably, the system includes a switch, such as a multiplexor, disposed between the transmission system, the receiver system and the ultrasound sensor array, and is coupled to the control system.

The adhesive patch preferably incorporates a wireless ultrasound system that is enabled by a miniaturized array of piezoelectric transducers. Such a device provides a wearable, continuous ultrasound solution for different applications such as diagnosis, monitoring the diagnosed body organs, rehabilitation and wound healing. In the diagnosis and monitoring mode, the system has the capability of recording and transmitting the characteristics of the medium/object, in the form of the amplitude, frequency and phase of the signal. These signals can further be interpreted as either an image or a sound signal. The resulting data can also be recorded on the patch for subsequent wireless or wired download/transmission and/or transmitted in real time wirelessly to a nearby portable device (e.g., mobile phone, personal digital assistant, personal computer, etc.) to perform analytics and visualization, and transmit the original data and/or analyzed information (wirelessly) to a network of backend servers for dissemination, analytics and visualization, and/or archiving. The patch's wireless communication capability also provides for bypassing the utilization of a nearby portable device and connecting directly to backend servers. Such an ultrasound patch can be utilized in a variety of applications depending on the required power, configuration, size and characteristics of the ultrasound transducers, which in turn dictate the depth of the ultrasound signal penetration, detection sensitivity and resolution, and system complexity. One key application area of interest for such an ultrasound patch is medical diagnostics and therapeutics. By its nature, the adhesive ultrasound patch is wearable and nonintrusive, thus presenting a significant advantage over existing medical ultrasound imaging and sensing devices.

The adhesive ultrasound patch, placed appropriately on a subject, enables continuous monitoring of the heartbeat without interfering with the subject's routine activities. Another example is nonintrusive monitoring of patients with known at-risk lesions in the carotid artery prior to, or post-heart surgery by placing the patch on the neck. Yet another application is for detection of the on-set of a stroke with electronic spatial scanning techniques while the patch is attached to the neck to monitor the lesions in the carotid artery. Another application is for continuous fetus heartbeat monitoring (especially for high risk pregnancies) when the patch is adhered to mother's belly. In addition, equipping the patch with dry electrodes enables recording the EMG signals associated with uterine contraction to enable synchronous monitoring of fetal heart rate and uterine contraction [23]. Therapeutic and rehabilitation examples would be placement of the patch over target nerves or painful joints (rheumatoid arthritis) for stimulation using the incident ultrasound wave energy. These measurements and diagnostics are enabled by using one or more ultrasound transducers. Transducer array architectures are often desired because they provide redundancy, ensuring functionality even if a subset of the transducer elements fails.

Today's technology trend is toward low-cost, miniaturized and user-friendly ultrasound devices. Having a nonintrusive, wearable, preferably low-cost ultrasound device is the subject of this disclosure. Such an ultrasound device, implemented as an adhesive patch, can be used for electronic spatial scanning using Doppler technique (e.g., for monitoring heart or carotid artery), virtual focusing and noise rejection (e.g., for fetus monitoring), as well as therapeutic and wound healing applications. While ultrasound techniques are utilized in modern ultrasound devices [12], [18] but a nonintrusive, wearable embodiment is not available. The ultrasound patch can also be used to monitor and hasten the healing of venous leg ulcers or internal wounds after surgery; in such an application, high-resolution imaging is not required.

DETAILED DESCRIPTION OF THE INVENTION

Common issues with ultrasound devices are the larger the size, the higher the power consumption and cost. In addition to the miniaturized size and ease of use of the proposed patch, the applications that this patch address are compelling in the sense that they do not necessarily require a high-resolution image, but rather characterizing the conditions of the tissue or medium under investigation or just providing ultrasound energy for therapeutic, rehabilitation, and assisting in the healing process.

Figure 1:
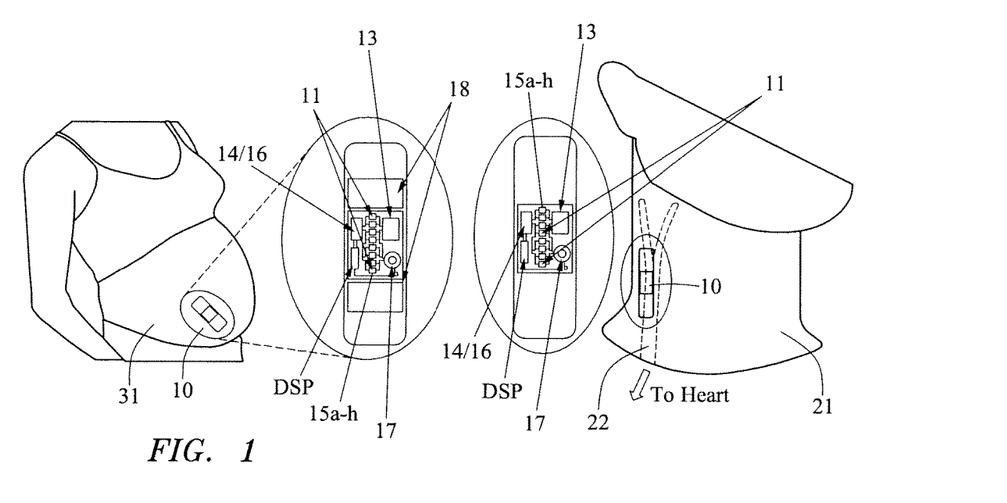
FIG. 1 is a perspective view of a wearable patch incorporating aspects of the invention.

In FIG. 1, an adhesive-patch embodiment is shown. The ultrasound device 10 is placed on a designated location and held in place tightly through a special bio-compatible adhesive. Strategic use of the adhesive optionally eliminates the need for application of a gel. For example, in case of monitoring arteries (FIG. 1, right hand side), continuous-wave Doppler ultrasound uses a processing technique to measure the speed and direction of blood flow in the monitored area. It first transmits a known signal, such as a pulse, and then receives the reflected waves and measures the Doppler shift, which is the change in frequency and phase of the reflected ultrasound signal, to determine the direction and rate of blood flow in vessels, veins, and arteries. This measurement technique more accurately diagnoses vascular conditions, or faulty valves and arteries in the heart. In FIG. 1 (left hand side) an ultrasound patch is used to monitor the fetal heart beat using the same Doppler Effect and measuring the changes in the frequency and phase of the reflected signal.

FIG. 1 shows the concept of utilizing a linear array 11 of miniaturized ultrasound transducers 15*a-h* built into an adhesive patch 10. FIG. 1 on the right shows monitoring the carotid artery 22 by positioning the ultrasound device 10 on the patient's neck 21; and on the left monitoring a fetal heartbeat by placing the ultrasound device 10 on the mother's stomach 31.

A linear array 11 of 2, 4 or 8 transducer elements 15*a-h* (e.g., Lead Zirconate Titanate (PZT)) may be used to sweep the targeted area with ultrasound waves. The penetration depth is dependent on the frequency of the signal. Hence for a few centimeter penetration depths (e.g., monitoring the carotid artery), a 1 MHz signal will be low loss and provides enough resolution, while keeping the measurement noise to a reasonable level. The maximum depth of penetration for this application is not more than a few centimeters and hence, this will provide enough information for monitoring. However, for fetal heartbeat monitoring, a higher frequency signal (about 2 MHz-10 MHz) is used, as it needs to penetrate deeper into the body, resulting in much more signal attenuation. Such an ultrasound patch can be utilized in a variety of applications depending on the required power, configuration, size and characteristics of the ultrasound transducers, which in turn dictate the depth of the ultrasound signal penetration, detection sensitivity and resolution, and system complexity [3]. Table 1 summarizes the absorption rates for ultrasound waves going through different medium/tissue.

TABLE 1

| Absorption coefficient (dB/cm-MHz) for different body organs [3]. |  |
| --- | --- |
| Blood | 0.18 |
| Fat | 0.63 |
| Liver | 1 |
| Muscle | 1.3-3.3 |
| Bone | 20 |
| Lung | 41 |

In a Doppler ultrasound, the measured shift in the frequency/phase of the received signal in comparison to the transmitted signal is of interest, even though it may be very small. This method is called continuous-wave (CW) Doppler, where the change in frequency and phase of the reflected ultrasound signal is measured. This technique is different from the traditional sonographic techniques and does not require the generation of an image. Preferably, it measures the flow in blood vessels, veins, and arteries (i.e., to help physicians in evaluating the body's circulatory system and assessing various conditions such as formation of blood clots, detection of narrowing or widening of vessels, etc.). In the case of carotid artery for example, sweeping a distance of about 2 cm on the artery using a sweeping angle of ±45° with about 15 times-per-second sampling rate is preferred (FIG. 2). Since the target is about a few centimeters deep and the loss of the signal traveling in the body is in the range of 1 dB/cm-MHz, the sensor delivers milli-watts of power at the desired frequency (1 MHz in this case).

As shown in FIG. 1, the ultrasound patch 10 includes a power source 13, such as a battery. The power source 13 may be of any kind known to those skilled in the art suitable for the instant purpose, whether rechargeable, replaceable, operating by direct connection or power scavenging, such as an inductively charged capacitor. A transmission system 14 is coupled to the ultrasound sensor array 11 to provide signal information for transmission to the patient's body. A receiver system 16 is coupled to the ultrasound sensor array 11 to receive signal information from the patient's body. The data can be recorded and subsequently downloaded via wireless link 17, or alternatively, the data may be transmitted in real time to an external device such as a nearby portable device via wireless link 17. In some embodiments, the patch 10 may further include electrodes 18 or other dry electrodes, for example to record bio-potentials such as electromyogram (EMG), electrocardiogram (ECG) or monitor tissue fluid retention.

Figure 2A:
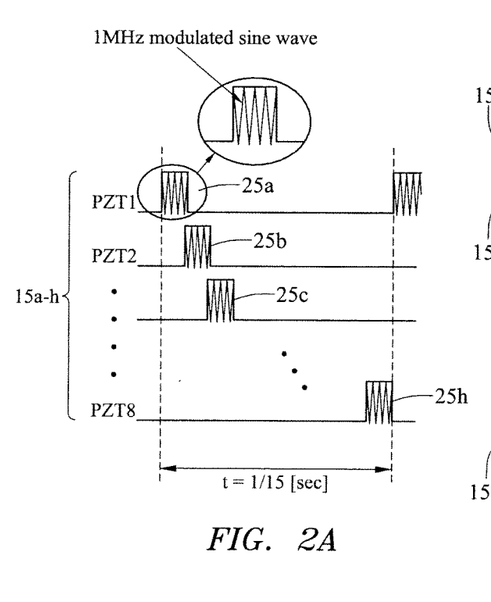
FIG. 2A shows waveform amplitude of pulses as a function of time.
Figure 2B:
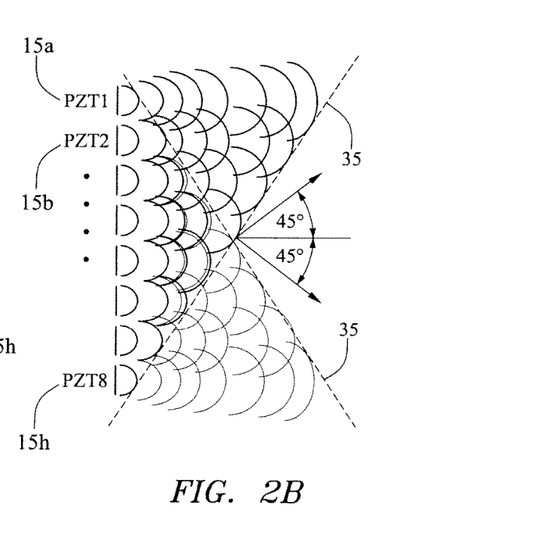
FIG. 2B shows the progression of waveforms resulting from the pulses of FIG. 2A.

FIG. 2A shows the waveform (ping) 25a-h on the eight ultrasound sensors 15a-h (e.g., PZT). FIG. 2B shows the creation of the wave front 35 by sweeping the waveform on the sensors 15a-h.

In choosing the transducer elements (e.g., PZT), the thickness of the material is important so that the element does not resonate at the frequency of operation (e.g., thickness should preferably be about $\lambda/2$; hence, for a PZT operating at 1 MHz, a thickness of about 2 mm would preferably be used).

Figure 3:
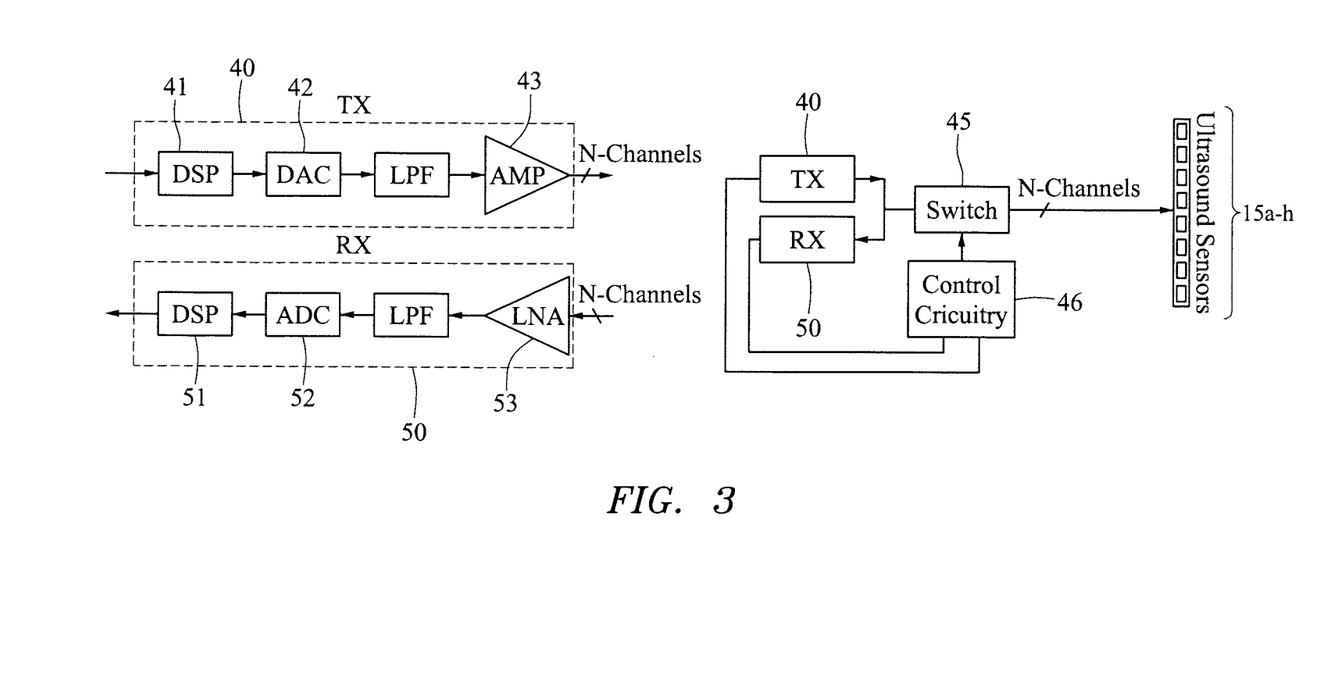
FIG. 3 shows simplified block diagram of the ultrasound analog front end circuitry.

FIG. 3 shows a block diagram of the analog front end for the continuous wave (CW) ultrasound system, where a switch 45 will select between the transmit 40 or receive 50 paths. In the transmission path 40, digital signal processing (DSP) 41 generates the digital signals to drive each transducer element 15a-h. These signals are converted to analog signals by a digital to analog convertor 42 and transmitted out using a power amplifier 43. In the receive path 50, the signals coming from each transducer element 15a-h are first reconditioned by a low-noise amplifier 53, next digitized by an analog to digital convertor 52 and then processed in digital domain by a digital signal processor 51 to produce the final results. This architecture may be implemented based on various implementation known to those skilled in the art of dealing with transmit (TX) and receive (RX) components. Each application will set the load requirements and needed actuations, hence choosing the power levels and the technology to implement the circuitry is case-based [20].

A control circuitry 46 is coupled to the transmission system 40 and the receiver system 50. The control system may include analytical or analysis functions. A processor may be provided, either within the patch, or external to the patch, to perform analytical or analysis functions.

Optionally, additional ultra-miniature and low-cost sensors or electrodes are integrated into the platform for expanded diagnostic capabilities. For example, microphones 113, 114 to hear other body sounds, such as heartbeat and lung sound, as well as fetal heartbeat monitoring, such as described in R. R. Lahiji, M. Mehregany, "Microphone Arrays for Listening to Internal Organs of the Body", U.S. Provisional Patent No. 61/258,082, filed November 2009, incorporated herein by reference as if fully set forth herein, may be incorporated into the patch 100, as shown in FIG. 4C. See also [21]. In addition, electrodes 18, preferably dry electrodes, to record bio-potentials such as electromyogram (EMG), electrocardiogram (ECG) or tissue fluid retention may be incorporated into the patch 10, for example as shown in FIG. 1.

Figure 4A:
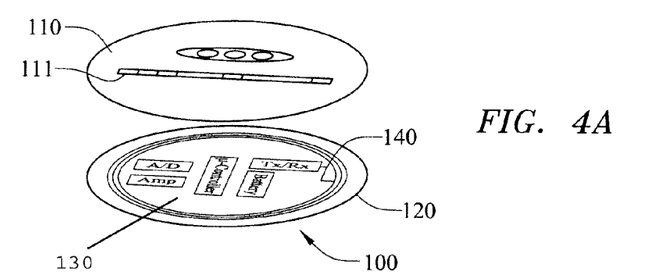
FIG. 4A shows a wearable adhesive patch comprising a top patch and a bottom patch and integrating both ultrasound transducers and microphones.
Figure 4B:
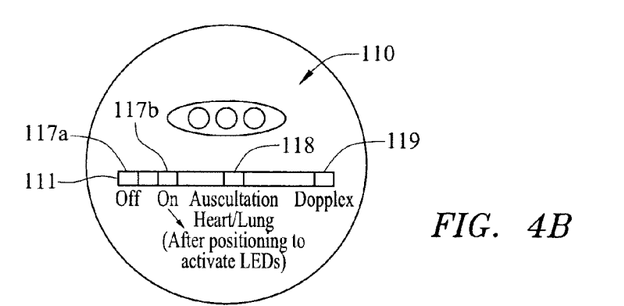
FIG. 4B shows a top view of the top patch having the user interface and optional mode selectors.
Figure 4C:
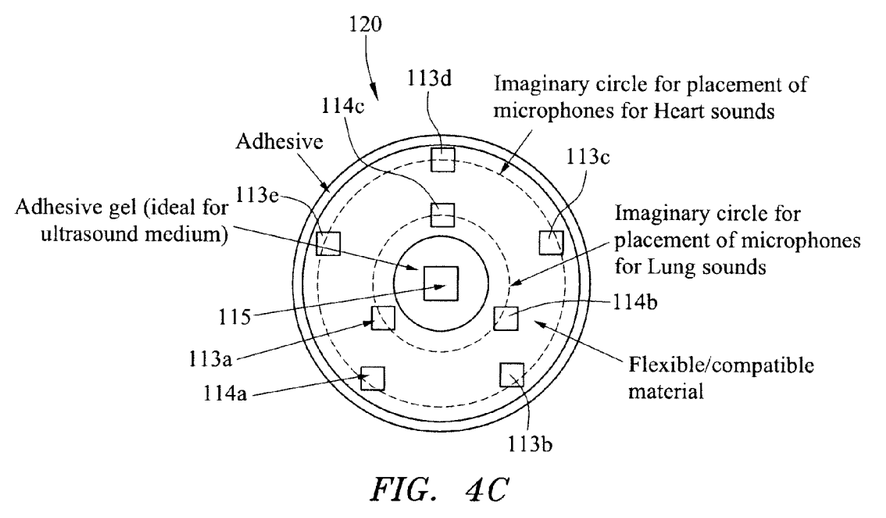
FIG. 4C shoes a bottom view of the bottom patch including both ultrasound transducers and microphones.

FIGS. 4A-C show a possible configuration for a multipurpose adhesive patch 100, integrating both microphones positioned to hear heart sounds 113a-e, microphones positioned to hear lung sounds 114a-c, and an array of ultrasound transducers 115 in a wearable patch 100. As shown in FIG. 4A, the ultrasound patch 100 may comprise a top patch 110 with the user interface 111 and a bottom patch 120 including the ultra sound sensors 115 and microphones 113a-h and 114a-c, for listening to heart sounds or lung sounds. In some embodiments, the circuit components and wiring 130 may be positioned in between the top patch 110 and bottom patch 120. Alternatively, a flexible printed circuit board 140 may be included on the bottom patch 120. As shown in FIG. 4B, the top view of the patch 110 is the side that faces the user and includes a user interface 120. Depending on the needed functionality, the user can turn the device On/Off 117a, b and select between the modes: auscultation of sounds of the body 118 or listening to the heartbeat 119, for example. Temperature sensors and accelerometers are among other possibilities, e.g., in a wearable, adhesive patch, one or more accelerometers can additionally capture the activity level of the person to help in additional assessment of health and well being.

In one implementation of the patch, the wearable patch for use on a body is in the form of a planar pad. The preferred dimensions of the patch are 80 mm×25 mm and thickness 5 mm or less, and most preferably 60 mm×20 mm 3.5 mm or less. The patch should be light-weight, about 16 grams or preferably weighing 8 grams or less.

In yet another aspect, the wearable patch for use on a body may transmit or receive signal information to and from the body (respectively) to communicate data, control signals and/or power to an implant or transient device within the body or receive data from such device; namely ultrasound radio. Exemplary implants include a pacemaker or an implanted pump. A transient device through the body, like a device incorporated in/on a pill swallowed, would be another example, in place of an implant.

In yet a further aspect, the wearable patch 100 may be removable from the remainder of the components. In this way, the outer portion (shell) 110, 120 comprising the patch 100 is disposable, while the inner (electronic and sensor) components 130 may be removed to possibly recharge, download the saved data or just reused using a fresh outer shell and adhesive. The patch may optionally include electrically conductive regions adapted to contact the body. The electrically conductive regions are adapted to contact electrically conductive regions within the patch.

Optionally, the wearable patch 100 may include a flexible printed circuit board 140. The flexible printed circuit board 140 permits more intimate contact of the patch 100 with the person, more easily conforming to the shape of the body.

All publications and patents cited in this specification are herein incorporated by reference as if each individual publication or patent application were specifically and individually indicated to be incorporated by reference. Although the foregoing invention has been described in some detail by way of illustration and example for purposes of clarity and understanding, it may be readily apparent to those of ordinary skill in the art in light of the teachings of this invention that certain changes and modifications may be made thereto without departing from the spirit or scope of the following claims.

REFERENCES

All of which are incorporated herein by reference as if fully set forth herein.

[1] B. H. Brown and et al., *Medical physics and biomedical engineering*, Taylor & Francis, Inc., October 2008.
[2] Casimiro L, Brosseau L, Robinson V, Milne S, Judd M, Well G, Tugwell P, Shea B., "Therapeutic ultrasound for the treatment of rheumatoid arthritis", Cochrane Database Syst Rev. 2002; (3):CD003787. Review. (PubMed PMID: 12137714).
[3] P. Å. Öberg, T. Togawa, F. A. Spelman, Series: Sensors Applications, "Sensors in Medicine and Health Care", Wiley-VCH, 2004.
[4] P. W. Henderson, G. K. Lewis, N. Shaikh, A. Sohn, A. L. Weinstein, W. L. Olbricht and J. A. Spector, "A portable high-intensity focused ultrasound device for noninvasive venous ablation", Journal of Vascular Surgery, in press 2010.
[5] Byl N N, McKenzie A, Wong T, West J, Hunt T K., "Incisional wound healing: a controlled study of low and high dose ultrasound", Journal of Orthop. Sports Phys. Therapy, 1993 November; 18(5):619-28.
[6] "Wound healing assessment using 20 MHz ultrasound and photography", Skin Research and Technology, J. Wiley & Sons A/S, Vol. 9 Issue 2, pp. 116-121, April 2003.
[7] B. P. Nelson, E. R. Melnick, J. Li, "Portable ultrasound for remote environments, part i: Feasibility of field deployment", The Journal of Emergency Medicine, Available online 25 Jan. 2010.
[8] L. Pelissier, B. Zhang, T. Bobovsky, "Highly Configurable Medical Ultrasound Machine and Related Methods", U.S. Pat. No. 0,049,050 A1, February 2010.
[9] F. H. Sheehan, M. A. Ricci, C. Murtagh, H. Clark and E. L. Bolson, "Expert visual guidance of ultrasound for telemedicine", Journal of Telemedicine and Telecare, No. 16, pp. 77-82, March 2010.
[10] GE, Ultrasound for vascular imaging at: http://www.ge-healthcare.com/usen/ultrasound/genimg/products/vascular.html as of April 2011.
[11] GE, Imaging at: https://www2.gehealthcare.com/portal/site/usen/menuitem.0668199d894d5150380617-1047b29330/?vgnextoid=dd3ba52fcea2d110VgnVCM-100000258c1403RCRD&vgnextfmt=default as of April 2011.
[12] Vscan, pocket sized ultrasound device unveiled by GE in October 2009 at: http://www.gereports.comJvscan-pocket-sized-ultra-smart-ultrasound-unveiled as of April 2011.
[13] Acuson P40 ultrasound system at: http://www.usedultrasound.com/ultrasound-systems/acuson/acuson-p10-ultrasound-system as of April 2011.
[14] GE, overview of Obstetrics Ultrasound products at: http://www.gehealthcare.com/usen/patient/ultrasound/aboutvoluson.html as of April 2011
[15] Fetal monitors at: http://www.advanced-pharma.com/fetalmonitors.html as of April 2011
[16] baby beat, hand held Doppler at: http://www.babybeat.com/about-babybeat.html as of April 2011
[17] Portable diagnostic ultrasound machines at: http://www.sonosite.com/products/portable-ultrasound/ as of April 2011.
[18] "Fitzpatrick, Tony, "*Ultrasound imaging now possible with a smartphone*," (Apr. 9, 2009) available at: http://news-info.wustl.edu/tips/page/normal/13928.html as of April 2011.
[19] Professional Ultrasound Unit for Ultrasound Therapy at: http://www.lgmedsupply.com/lgpoulun.html as of April 2011
[20] B. Haider, "Power Drive Circuits for Diagnostic Medical Ultrasound", Proceedings of the 18th International Symposium on Power Semiconductor Devices & IC's, June 2006.
[21] R. Miller, "Two-mic system detects fetal heart rate anomalies, prenatal beat sampling," at: http://www.engadget.com/2009/08/30/two-mic-system-detects-fetal-heart-rate-anomalies-prenatal-beat as of April 2011.
[22] D. Schlembach, W. L. Maner, R. E. Garfield, H. Maul, "Monitoring the Progress of Pregnancy and Labor using Electromyography", European Journal of Obstetrics & Gynecology and Reproductive Biology, Vol. 144, Supp. 1, pp. S33-S39, May 2009.

What is claimed:

1. An integrated wearable device for use on a maternal body including at least one fetus to detect sounds which are indicative of a fetal heart rate and biopotentials indicative of maternal uterine contractions and for wireless communication to a local wireless communications device the wireless communications device providing for data visualization relating to fetal heart rate and maternal uterine contractions, comprising:

an adhesive planar, flexible patch, the patch having a center, the adhesive patch adapted for attachment to the maternal body, an ultrasound transducer array, the ultrasound transducer array being an array located at the center of the patch composed of a plurality of transducer elements, the ultrasound transducer array being supported by the patch to maintain the ultrasound transducer array in an operative contacting relationship to the maternal body for detection of at least signals indicative of the fetal heart rate, a transmission system coupled to the ultrasound transducer array to provide signal information for transmission into the maternal body using the ultrasound array, a planar microphone array, the microphone array including a first plurality of microphones being arranged in a first circular array located a first fixed distance from the center of the planar, flexible patch, and a second plurality of microphones being arranged in a second circular array located a second fixed distance from the center of the patch, where the first fixed distance and second fixed distance are different, the microphone array being positioned to be placed in operative contacting relationship to the maternal body for detection of at least signals indicative of the fetal heart rate, a receiver system coupled to the ultrasound microphone array to receive signal information including both frequency and phase information at least indicative of the fetal heart rate through the ultrasound array, a continuous wave Doppler detector, the detector coupled to the receiver system to utilize both frequency and phase of the received signal information to determine the fetal heart rate, two or more electrodes, the electrodes being supported by the patch to maintain the electrodes in an operative relationship to the maternal body for detection of at least biopotential signals indicative of maternal uterine contractions, a switch disposed between the (1) transmission system and receiver system and (2) the ultrasound array, control circuitry coupled to the transmission system and the receiver system to selectively actuate the switch between transmitting and receiving signals through the ultrasound transducer array and the microphone array, the control circuitry further including an analytics processor to determine the fetal heart rate and maternal uterine contractions, and, a wireless communication system, the wireless communication system sending the information relating to the signals indicative of the fetal heart rate and the biopotential signals indicative of maternal uterine contractions to the local wireless communications device in real time for data visualization relating to fetal heart rate and maternal uterine contractions.

2. The wearable device for use on a maternal body of claim 1 wherein the ultrasound transducer array has at least 2 transducer elements arranged in a linear manner.

3. The wearable device for use on a maternal body of claim 1 wherein the ultrasound transducer array has at least 4 transducer elements arranged in a linear manner.

4. The wearable device for use on a maternal body of claim 1 wherein the ultrasound transducer array has at least 8 transducer elements arranged in a linear manner.

5. The wearable device for use on a maternal body of claim 1 wherein the transmission system includes an amplifier adapted to receive an input from the control system.

6. The wearable device for use on a maternal body of claim 5 wherein the transmission system further includes a digital to analog converter disposed between the control system and the amplifier.

7. The wearable device for use on a maternal body of claim 6 wherein the transmission system further includes a digital signal processor between the control system and the digital to analog converter.

8. The wearable device for use on a maternal body of claim 1 wherein the receiver system includes an amplifier.

9. The wearable device for use on a maternal body of claim 8 wherein the amplifier is a low noise amplifier.

10. The wearable device for use on a maternal body of claim 8 wherein the transmission system further includes an analog to digital converter coupled to the amplifier.

11. The wearable device for use on a maternal body of claim 10 wherein the transmission system further includes a digital signal processor coupled to the digital to analog converter.

12. The wearable device for use on a maternal body of claim 1 wherein the switch is a multiplexor switch.

13. The wearable device for use on a maternal body of claim 1 wherein the adhesive patch includes a biocompatible adhesive.

14. The wearable device for use on a maternal body of claim 1 wherein the ultrasound transducer array includes piezoelectric transducers.

15. The wearable device for use on a maternal body of claim 14 wherein the piezoelectric transducers are lead zirconate titanate piezoelectric transducers.

16. The wearable device for use on a maternal body of claim 1 wherein the received signal information is analyzed for blood flow within the body.

17. The wearable device for use on a maternal body of claim 1 further including at least one microphone.

18. The wearable device for use on a maternal body of claim 17 wherein the microphone is adapted to receive auscultator sounds.

19. The wearable device for use on a maternal body of claim 1 wherein the biopotential is an electromyogram (EMG).

20. The wearable device for use on a maternal body of claim 1 further including at least one temperature sensor.

21. The wearable device for use on a maternal body of claim 1 further including at least one accelerometer.

22. The wearable device for use on a maternal body of claim 1 further including at least one mode switch.

23. The wearable device for use on a maternal body of claim 1 wherein the thickness of the patch is 3.5 mm or less.

24. The wearable device for use on a maternal body of claim 1 wherein the weight of the patch is 8 grams or less.

25. The wearable device for use on a maternal body of claim 1 wherein the signal information transmitted to the body provides information to an implant within the body.

26. The wearable device for use on a maternal body of claim 1 wherein the patch is removable from the remainder of the components.

27. The wearable device for use on a maternal body of claim 26 wherein patch is disposable.

28. The wearable device for use on a maternal body of claim 1 wherein the patch includes a flexible printed circuit board.

29. The wearable device for use on a maternal body of claim 1 wherein the wireless communications device is a mobile phone.

30. The wearable device for use on a maternal body of claim 1 wherein the wireless communications device is a personal digital assistant.

31. The wearable device for use on a maternal body of claim 1 wherein the wireless communications device is a personal computer.

32. The wearable device for use on a maternal body of claim 1 further including a server adapted to communicate with the wireless communications device.

* * * * *